(12) United States Patent
Schuler et al.

(10) Patent No.: US 8,603,815 B2
(45) Date of Patent: *Dec. 10, 2013

(54) CD4+ CD25- T CELLS AND TR1-LIKE REGULATORY T CELLS

(75) Inventors: Gerold Schuler, Spardorf (DE); Detlef Dieckmann, Uttenreuth (DE)

(73) Assignee: Argos Therapeutics, Inc., Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/289,409

(22) Filed: Nov. 4, 2011

(65) Prior Publication Data

US 2012/0114597 A1    May 10, 2012

Related U.S. Application Data

(60) Continuation of application No. 11/765,720, filed on Jun. 20, 2007, now Pat. No. 8,076,134, which is a division of application No. 10/618,134, filed on Jul. 11, 2003, now Pat. No. 8,222,033.

(60) Provisional application No. 60/419,177, filed on Oct. 17, 2002.

(30) Foreign Application Priority Data

Aug. 12, 2002    (EP) .................................. 02018025

(51) Int. Cl.
*C12N 5/071*    (2010.01)
*C12N 5/00*    (2006.01)
*C12N 5/02*    (2006.01)
*A01N 63/00*    (2006.01)

(52) U.S. Cl.
USPC .................. 435/372.3; 435/373; 424/93.71

(58) Field of Classification Search
None
See application file for complete search history.

(56) References Cited

U.S. PATENT DOCUMENTS

| | | | |
|---|---|---|---|
| 5,721,910 A | 2/1998 | Unger et al. | |
| 5,752,020 A | 5/1998 | Ando | |
| 5,950,214 A | 9/1999 | Rivette et al. | |
| 5,991,751 A | 11/1999 | Rivette et al. | |
| 5,991,780 A | 11/1999 | Rivette et al. | |
| 5,999,907 A | 12/1999 | Donner | |
| 6,014,663 A | 1/2000 | Rivette et al. | |
| 6,038,561 A | 3/2000 | Snyder et al. | |
| 6,534,055 B1 | 3/2003 | June et al. | |
| 6,803,036 B1 | 10/2004 | Horowitz | |
| 7,479,269 B2 | 1/2009 | June et al. | |
| 2001/0003746 A1 | 6/2001 | Sodemann | |
| 2001/0003950 A1 | 6/2001 | Zhang et al. | |
| 2002/0090357 A1 | 7/2002 | Barrat et al. | |
| 2003/0005085 A1 | 1/2003 | Matsuno | |
| 2003/0013540 A1 | 1/2003 | Penrose | |
| 2003/0014491 A1 | 1/2003 | Horvitz et al. | |
| 2004/0147021 A1 | 7/2004 | Schuler et al. | |
| 2005/0101012 A1 | 5/2005 | Schuler et al. | |

FOREIGN PATENT DOCUMENTS

| | | |
|---|---|---|
| EP | 1 379 625 A1 | 1/2004 |
| EP | 1 409 650 B1 | 4/2006 |
| WO | 91 00345 A | 1/1991 |
| WO | 92 11348 A | 7/1992 |
| WO | 93 02108 A | 2/1993 |
| WO | 95 07991 A | 3/1995 |
| WO | 96 09396 A | 3/1996 |
| WO | 98 56417 A | 12/1998 |
| WO | 00 42856 | 7/2000 |
| WO | 02 097070 | 12/2002 |

OTHER PUBLICATIONS

O'Doherty et al., 1994, Immunology, vol. 82: 487-183.*
Cavani et al., 2000, J. Invest. Derm VOI. 14: 295-302.*
Alberts et al., eds., Molecular Biology of the Cell, 3rd edition (1994), pp. 142, 157, 158, 748, 749, and 853 (Garland Publishing, Inc., New York, NY, USA).
Ferlin et al., "Present difficulties and future promise of MHC multimers in autoimmune exploration," Curr. Opin. Immunol. (2000) pp. 670-675, vol. 12.
Goldsby et al., eds., Kuby Immunology, 4th edition (2000), pp. 203-206 and 513 (W.H. Freeman and Co., New York, NY).
Haskins et al., "The major histocompatibility complex-restricted antigen receptor on T cells," J. Exp. Med. (1983) pp. 1149-1169, vol. 157.
Mestas and Hughes, "Of mice and not men: differences between mouse and human immunology," J. Immunol. (2004) pp. 2731-2738, vol. 172.
Ribas et al., "Genetic Immunotherapy for Cancer," The Oncologist (2000), pp. 87-98, vol. 5.
Takahashi et al., "Immunologic self-tolerance maintained by CD25+ CD4+ naturally anergic and suppressive T cells . . . ," Int'l. Immunol. (1998) pp. 1969-1980, vol. 10.
Office Action mailed Aug. 31, 2010, for copending U.S. Appl. No. 10/661,804.
Office Action mailed Oct. 25, 2010, for copending U.S. Appl. No. 10/618,134.
Stout et al, 1993, J. Immunol. vol. 150: 5330-5337.
Milteny product information, CD25 microbeads, 2007, pp. 1-3.
Koulis et al, Feb. 2001, Allergy Clin Immunol. vol. 107, p. S294-S295.
Nakamura et al., 2001, J. Exp. Med. vol. 194: 629-644.
Jonuleit et al., Jul. 15, 2002, J. Exp. Med., vol. 196: 255-260.
Baecher-Allan et al., 2001, J. Immunol., vol. 167: 1245-1253.
Office Action issued on May 5, 2006 by Examiner for corresponding U.S. Appl. No. 10/661,804.
Office Action issued on Nov. 30, 2006 by Examiner for corresponding U.S. Appl. No. 10/661,804.
Office Action issued on Mar. 15, 2007 by Examiner for corresponding U.S. Appl. No. 10/661,804.

(Continued)

*Primary Examiner* — Amy Juedes
(74) *Attorney, Agent, or Firm* — Norris, McLaughlin & Marcus, P.A.

(57) ABSTRACT

The invention provides CD4+CD25- T cells and Tr1-like regulatory T cells (i.e., contact-independent Type 1-like regulatory T cells), processes for their production and their use for regulatory purposes.

4 Claims, 5 Drawing Sheets

(56) References Cited

OTHER PUBLICATIONS

Office Action issued on Aug. 8, 2007 by Examiner for corresponding U.S. Appl. No. 10/661,804.
Office Action issued on Mar. 31, 2008 by Examiner for corresponding U.S. Appl. No. 10/661,804.
Office Action issued on May 22, 2009 by Examiner for corresponding U.S. Appl. No. 10/661,804.
Office Action issued on Apr. 20, 2006 by Examiner for corresponding U.S. Appl. No. 10/618,134.
Office Action issued on Dec. 21, 2006 by Examiner for corresponding U.S. Appl. No. 10/618,134.
Office Action issued on Aug. 7, 2007 by Examiner for corresponding U.S. Appl. No. 10/618,134.
Office Action issued on Jul. 1, 2008 by Examiner for corresponding U.S. Appl. No. 10/618,134.
Office Action issued on Mar. 16, 2009 by Examiner for corresponding U.S. Appl. No. 10/618,134.
Taylor et al, Immunology and Cell Biology (2001) 79, 358-367.
Levings, M. et al., J. Exp. Med., 193: 1295-1301 (2001).
Fujimaki, W. et al., Clin. Develop. Immunol., 2008: 1-12 (2008).
Ng, W. et al., BSI Congress 2000, vol. 101, Supplement 1, Abstract 3.12 (2000).
Taams, L. et al., BSI Congress 2000, vol. 101, Supplement 1, Abstract IS6 (2000).
Ng. W. et al., Blood, 98: 2736-2744 (2001).
Taams, L. et al., Eur. J. Immunol., 31: 1122-1131 (2001).
Horwitz, D. et al., Arthrit. Research, 4: 241-246 (2002).
Read, S. et al., J. Exp. Med., 192: 295-302 (2000).
Olivares-Villagomez, D. et al., J. Immunol., 164: 5499-5507 (2000).
Sakaguchi, S., Cell, 101: 455-458 (2000).
Stephens, L. et al., Eur. J. Immunol., 31: 1247-1254 (2001).
Nagahama, K. et al., Methods Molecul. Biol., 380: 431-442 (2007).
Bacchetta et al, "High levels of interleukin-10 production in vivo are associated with tolerance in SCID patients . . . ", J. Exp. Med. (1994) pp. 493-5-2, vol. 179.
Cottrez et al,., "Specialization in tolerance: innate CD(4+) CD(25+) versus acquired TRI and TH3 regulatory cells", Transplantation (2004) pp. S12-S16, vol. 77.
Dieckmann et al., "Ex vivo isolation and characterization of CD4+ CD25+ T cells with regulatory properties from human blood,"J. Exp. Med. (2001) pp. 1303-1310, vol. 193.
Jackson et al., "Restricted expression of p55 interleukin 2 receptor (CD25) on normal T cells,"Immunol. Immunopathol. (1990) ;ages 126-133, vol. 54.
Kanegane et al., "A novel subpopulation of CD15RA+ CD4+ T cells expressing IL-2 . . . ," Int. immunol. (1991) pp. 1349-1356, vol. 3.
Rohowsky-Kochan et al., "Cytokine secretion profile of myelin basic protein-specific T cells in multiple sclerosis,"Multiple Sclerosis (2001) pp. 69-77, vol. 6.
Thornton et al. "Suppressor effector Function of CD4+ CD 25+ Immunoregulatory T Cells . . . " J. Immunol. (2000) pp. 183-190, vol. 164.
Jago et al., Diffenential expression of CTLA-4 among T cell subsets, Clin. Exp. Immunol. (2004) pp. 463-471, vol. 136.
Leung et al., "Cytotoxic T lymphocyte-associated molecule-4, a high avidity receptor . . . ," J. Biol. Chem. (1995) pp. 25107-25114, vol. 270.
Office Action mailed Feb. 19, 2010, for copending U.S. Appl. No. 10/661,804.
Office Action mailed Oct. 15, 2009, for copending U.S. Appl. No. 10/618,134.
Office Action mailed Feb. 3, 2010, for copending U.S. Appl. No. 10/618,134.
Office Action mailed Mar. 16, 2010, for copending U.S. Appl. No. 10/618,134.
Lechler et al., 2001, Phil. Trans. R. Soc. Lond. vol. 356: 625-637.
Chen et al., 2003, J. Exp. Med. vol. 198: 1875-1886.
Groux et al., 1997, Nature, vol. 389: 737-742.
Takahata et al., 2004, Exp. Hem. vol. 32: 622-629.
Levings et al., May 2001, J. Immunol. vol. 166: 5530-5539.
Dickmann D. et al., "Human CD4+CD25+ Regulatory, Contact-dependent T Cells Induce Interleukin 10-producing, Contact-independent Type 1-like Regulatory T Cells", The Journal of Experimental medicine, vol. 196, No. 2; Jul. 15, 2002; pp. 247-253; XP002239198.
Taylor et al, "T regulatory cells and allergy", Microbes and Infection 2005; 7: 1049-1055.
Thorn et al; "CD4+CD25+ immunoregulatory T cells suppress polyclonal T cells activation invitro by inhibiting interleukin 2 production". The Journal of Exp. Med. 1998; 188: 227-296.
Huang Z., "Structural chemistry and therapeutic intervention of protein-protein interactions in immune response, human immunodeficiency virus entry, and apoptosis.", Pharmacol Ther. Jun. 2000; 86 (3): 201-15.
Metler et al; "Solution structure of human CTLAM and delineation of a CD80/CD86 binding site conserved in CD28." Nat. Struct. boil. Jul. 1997; 4(7): 527-31.
Brode et al., Journal of Cellular Biochemistry, vol. 15, Part G., Apr. 8, 1991, p. 205.
DeJong et al; "Differential effect of transforming growth factor-$\beta 1$ on the activation of human naïve and memory CD4 + T lymphocytes," International Immunology, vol. 6, No. 4, pp. 631-638 (Jan. 1994).
Jonuleit et al.; "Induction of interleukin 10-producing, Nonproliferating CD4+ T Cells with Regulatory Properties by Repetive Stimulation with Allogneic Immature Human Dendritic Cells," J. Exp. Med., vol. 192, No. 9, pp. 1213-1222 (Nov. 6, 2000).
Shimizu et al., "Induction of tumor immunity by removing CD25+CD4+ regulatory T cells: A common basis between tumor immunity and autoimmunity," J. Immunol., vol. 163, No. 10, pp. 5211-5218 (1999).
Takahashi et al., "Immunologic self-tolerance maintained by CD25+CD4+ regulatory T cells consitutively expressing cytotoxic T lymphocyte-associated antigen 4"; J. Exp. Med. vol. 192, No. 2, pp. 303-309 (Jul. 17, 2000).

* cited by examiner

CD4+ CD25- T CELLS AND TR1-LIKE REGULATORY T CELLS

This application is a Continuation of U.S. patent application Ser. No. 11/765,720, filed Jun. 20, 2007, now allowed, which is a Division of U.S. patent application Ser. No. 10/618,134, filed Jul. 11, 2003, pending, which claims priority of U.S. Provisional Patent Application No. 60/419,177, and claims foreign priority benefit under 35 U.S.C. §119 of European Patent Application No. 02018025.3 filed Aug. 12, 2002, the disclosures of which are incorporated herein by reference.

The invention provides CD4+CD25- T cells and Tr1-like regulatory T cells (i.e., contact-independent Type 1-like regulatory T cells), processes for their production and their use for regulatory purposes.

INTRODUCTION

There is now compelling evidence that CD4+ T cells specialized for the suppression of immune responses play a critical role in immune regulation. It has been convincingly demonstrated in rodents, that cells with this function are enriched within the CD4+CD25+ subset (Asano et al., *J. Exp. Med.* 184:387-396 (1996); Takahashi et al., *Int. Immunol.* 10:1969-1980 (1998); Thornton et al., *J. Exp. Med.* 188:287-296 (1998)). Recent studies demonstrate, that CD4+ CD25+ T cells are also relevant as an immune regulator in humans (Jonuleit et al., *J. Exp. Med.* 193:1285-1294 (2001); Levings et al., *J. Exp. Med.* 193:1295-1302 (2001); Dieckmann et al., *J. Exp. Med.* 193:1303-1310 (2001); Taylor et al., *J. Exp. Med.* 193:1311-1318 (2001)). It was shown, that CD4+ CD25+ T cells, similar to their rodent counterpart, constitute a small fraction of CD4+ T cells (average 6%). They are naturally anergic to mitogenic stimuli, inhibit the proliferation of CD4+ and CD8+ T cells after stimulation via their TCR and do so in a cytokine-independent yet cell contact-dependent manner (Jonuleit et al., *J. Exp. Med.* 193:1285-1294 (2001); Levings et al., *M. Exp. Med.* 193:1295-1302 (2001); Dieckmann et al., *J. Exp. Med.* 193:1303-1310 (2001); Taylor et al., *J. Exp. Med.* 193:1311-1318 (2001)).

Progress has been made to elucidate the mechanisms by which CD4+CD25+ T cells exert their regulatory function. It has been suggested, that CD4+CD25+ T cells bind transforming growth factor β on their cell surface and thereby mediate contact dependent suppression of other T cells (Nakamura et al., *J. Exp. Med.* 194:629-644 (2001)). Two groups have described the increased expression of glucocorticoid-induced TNF receptor (GITR) on CD4+CD25+ T cells compared to resting CD4+CD25- T cells and they show, that anti-GITR antibodies abrogate CD4+CD25+ mediated suppression (Shimizu et al., *Nat. Immunol.* 3:135-142 (2002); McHugh et al., *Immunity.* 16:311-323 (2002)).

Very little is still known about requirements for the development and physiological regulation of CD4+ CD25+ T cell function. Survival and/or expansion of CD4+ CD25+ T cells in the periphery seems to be dependent on IL-2 and costimulatory molecules, as mice lacking these components show major deficiencies in CD4+CD25+ T cells (Papiernik et al., *Int. Immunol.* 10:371-378 (1998); Salomon et al., *Immunity.* 12:431-440 (2000); Kumanogoh et al., *J. Immunol.* 166:353-360 (2001)). It is difficult to understand, how CD4+CD25+ T cells exert their suppressive function in vivo, as they constitute only 6% of CD4+ T cells and need direct cell contact and activation via their TCR to suppress other T cells. In in vitro experiments usually rather high ratios of CD4+CD25+ T cells have to be employed to potently suppress proliferation of CD4+CD25- T cells. These are conditions, that probably would not occur in vivo, as CD4+CD25+ T cells even if antigen-specifically activated do not expand and proliferate well due to their anergic state. It has been shown before, that anergized T cells can mediate regulatory function on other T cells (Jooss et al., *Proc. Natl. Acad. Sci. U.S.A.* 98:8738-8743 (2001)). It was now found that CD4+CD25+ T cells do not only anergize other CD4+ T cells, but that they also induce high level production of IL-10 in the cells they suppress. The resulting IL-10 producing anergized T cells are then able to suppress T cell proliferation in an IL-10 dependent fashion. These findings give insight into the mechanisms utilized by CD4+CD25+ T cells to execute their important in vivo function.

SUMMARY OF THE INVENTION

It has been recently demonstrated that regulatory CD4+CD25+CD45RO+ T cells are present in the peripheral blood of healthy adults and exert regulatory function similar to their rodent counterparts (PCT/EP02/02671). It remains difficult to understand how the small fraction of these T cells, that regulate via direct cell-to-cell contact and not via secretion of immunosuppressive cytokines, could mediate strong immune suppression.

It was now found that human CD4+CD25+ T cells induce long lasting anergy and production of Interleukin-10 in CD4+CD25- T cells. These anergized CD4+CD25- T cells then suppress proliferation of syngeneic CD4+ T cells via Interleukin-10 but independent of direct cell contact, similar to the so-called type 1 regulatory T cells (Tr1). This "catalytic" function of CD4+CD25+ T cells to induce Tr1-like cells helps to explain their central role for the maintenance of immune homeostasis. The invention thus provides (1) CD4+CD25- T cells being able to exert contact-independent regulatory functions;

(2) Tr1-like regulatory T cells (also designated "contact-independent Type 1-like regulatory T cells") which are obtainable by anergizing the CD4+CD25- T cells according to (1) above, preferably by contact with CD4+CD25+ T cells, and exert contact-independent regulatory functions;

(3) a method for expanding CD4+CD25- T cells as defined in (1) above or Tr1-like regulatory T cells as defined in (2) above, which method comprises stimulating the T cells with a T cell stimulating agent or with antigen-presenting cells ex vivo and in vivo;

(4) a method for producing the Tr1-like regulatory T cells of (2) above, which method comprises anergizing CD4+CD25- T cells as defined in (1) above or as obtained by the method of (3) above by contacting the CD4+CD25- T cells with an anergic state inducing agent ex vivo and in vivo;

(5) Expanded CD4+CD25- T cells and expanded Tr1-like regulatory T cells obtainable by the method according to (3) above and Tr1-like regulatory T cells obtainable by the method according to (4) above;

(6) a pharmaceutical composition comprising the human CD4+CD25- T cells or Tr1-like regulatory T cells according to (1), (2) or (5) above;

(7) the use of CD4+CD25- T cells or of Tr1-like regulatory T cells according to (1), (2) or (5) above
 (a) for preparing a regulatory medicament;
 (b) in assays that will allow to identify other regulatory factors;
 (c) for identifying molecules expressed by the CD4+CD25- T cells or by the Tr1-like regulatory T cells including identification of novel molecules on said cells;

(d) for identifying precursor cells or progeny of the regulatory CD4$^+$CD25$^-$ T cells or of the Tr1-like regulatory T cells;

(e) for preparing an agent for adoptive transfer therapy, an agent for treating diseases with enhanced immunity including but not limited to autoimmune diseases, or an agent for preventing/treating transplantation reactions such as graft versus host disease, graft rejections, etc;

(8) the use of an anergic state inducing agent as defined in (4) above for preparing an agent to induce Tr1-like regulatory T cells in vivo, preferably for preparing an agent for treating autoimmune diseases in a patient;

(9) a method for adoptive transfer therapy which comprises injecting/infusing back into the patients enriched/expanded autologous or non-autologous Tr1-like regulatory T cells according to (2) or (5) above;

(10) a method for preparing CD4$^+$CD25$^-$ T cells and Tr1-like regulatory T cells with a particular desired antigen-specific T cell receptor which comprises (i) activating/stimulating/expanding the CD4$^+$CD25$^-$ T cells according to (1) above or the Tr1-like regulatory T cells according to (2) above with antigen presenting cells, preferably immature or mature dendritic cells (DC), presenting said antigen in vitro or in vivo, or (ii) utilizing a ligand/antibody to a particular T cell receptor expressed on (subsets of) CD4$^+$CD25$^-$ regulatory T cells or Tr1-like regulatory T cells, or a MHC-peptide complex binding to a particular T cell receptor on (subsets of) CD4$^+$CD25$^-$ T cells or Tr1-like regulatory T cells, and optionally, in case of CD4$^+$CD25$^-$ T cells, anergizing said CD4$^+$CD25$^-$ T cells by contacting them with an anergic state inducing agent;

(11) CD4$^+$CD25$^-$ T cells and Tr1-like regulatory T cells having a particular desired antigen-specific T cell receptor and being obtainable by (i) the method of (10) above, or by transfection of a T cell receptor of desired antigen specificity into ex vivo isolated or expanded T cells; or (ii) by the method of (10) above, and which have been brought in anergic state according to the method of (4) above;

(12) a pharmaceutical composition comprising the T cells of (11) above, preferably said pharmaceutical composition being suitable to treat diseases with enhanced immunity including, but not limited to, autoimmune diseases, graft versus host disease and graft rejections; and (13) the use of agents specifically binding to defined entities on the Tr1-like regulatory T cells, including but not limited to ligands/antibodies, such as monoclonal antibodies or MHC-peptide complexes or other ligands binding to T cell receptors on (subsets of) the Tr1-like regulatory T cells for preparing a medicament for removal or functional impairment of Tr1-like regulatory T cells in vivo in order to enhance immune responses, including dampen regulation by and Tr1-like regulatory T cells in vivo, for example, to enhance tumor immunity.

DESCRIPTION OF THE FIGURES

(A) After various time points supernatants were analyzed for cytokine production by ELISA. IL-10 production peaked 48 h after onset of culture and was markedly higher in the coculture of CD4$^+$CD25$^+$ and CD4$^+$CD25$^-$ T cells then in the cultures of each of the cell types alone. A representative out of 5 independent standardized experiments is shown. No elevated levels of INF-α or TGF-β could be measured (data not shown).

(B) The different T cell populations were also activated with mature allogeneic DC (DC:T cell ratio 1:20) compared to anti-CD3 and anti-CD28 (10 µg/ml respectively). Cytokines were measured 48 h after onset of culture. Results were similar in 5 independent experiments.

(C) For the last 6 h of activation with anti-CD3 and anti-CD28 2 µM Monensin was added to the cultures. Staining of CD4 surface expression was performed. Cells were washed, fixed, permeabilized and stained for intracellular IL-10 using PE-conjugated specific Abs. One of 5 independent experiments is shown.

(A) CD4$^+$ T cell subpopulations were sorted by MACS® CD4$^+$CD25$^+$ T cells were divided into 3 fractions. One part was activated with platebound anti-CD3 (10 µg/ml) and soluble anti-CD28 (10 µg/ml) over night and fixed next day with paraformaldehyde 2% (activated-fixed). The second part was fixed with paraformaldehyde without activation (resting-fixed) and the second part was left untreated (viable). Each fraction was mixed with syngeneic CD4$^+$CD25$^-$ T cells at a 1:1 ratio (10$^5$ T cells per 96 well) and stimulated with plate-bound anti-CD3 (10 µg/ml) and soluble-anti-CD28 (10 µg/ml). Proliferation was determined by [$^3$H]Tdr incorporation after 5 d. Results are representative of 5 independent experiments, shown as mean cpm of triplicate cultures. Similar results were observed, when T cells were stimulated with mature allogeneic DC (DC/T cell ratio of 1:20; data not shown).

(B) CD4$^+$CD25$^+$ and CD4$^+$CD25$^-$ T cells were either cultured alone or CD4$^+$CD25$^-$ T cells were mixed at a 1:1 ratio with activated-fixed, resting-fixed or viable CD4$^+$CD25$^-$ T cells. T cells were stimulated with mature allogeneic DC at the same ratio as in (A). In a parallel transwell approach CD4$^+$CD25$^+$ T cells were stimulated with allogeneic DC (DC/T ratio 1:20) in a transwell chamber, and CD4$^+$CD25$^-$ T cells were placed in the well together with allogeneic DC again at a DC/T ratio of 1:20. IL-10 production was measured by ELISA 48 h after onset of culture. Results were similar in 5 independent experiments.

FIG. 3: CD4$^+$CD25$^-$ T cells anergized by CD4$^+$CD25$^+$ T cells suppress proliferation of CD4$^+$ T cells in a IL-10 dependent manner. MACS® sorted CD4$^+$CD25$^+$ and CD4$^+$CD25$^-$ T cells were either cultured alone or mixed at a 1:1 ratio (2×10$^6$ T cells/24 well) and stimulated with mature allogeneic DC (DC/T cell ratio 1:20) or immobilized anti-CD3/soluble anti-CD28. After 48 h of culture cells were harvested and one fraction of each population was fixed with paraformaldehyde for 1 h. Viable and fixed cells were cocultured with syngeneic resting CD4$^+$CD25$^-$ T cells at a 1:1 ratio (10$^5$ T cells per 96 well) and stimulated as before with immobilized anti-CD3/soluble anti-CD28 (lower panel) or mature allogeneic DC (upper panel) in the presence or absence of 10 µg/ml anti-IL-10 antibodies. In a parallel transwell approach the three different T cell populations were placed in a transwell chamber and resting CD4$^+$CD25$^-$ T cells were stimulated with DC (DC/T cell ratio 1:20; upper panel) or platebound anti-CD3/soluble anti-CD28 (lower panel) in the well. Proliferation after 5 d was determined by [$^3$H]Tdr incorporation. One out of 4 independent experiments is shown.

FIG. 4: (A) Anergized CD4$^+$CD25$^-$ T cells predominantly secrete IL-10. CD4$^+$CD25$^+$ and CD4$^+$CD25$^-$ T cells were isolated as described and stimulated alone or at a 1:1 ratio with anti-CD3/anti-CD28. 48 h after stimulation supernatant was harvested and analyzed by a cytometric bead array for IL-2, IL-4, IL-5, TNF-α and INF-γ. Results were similar in 5 independent experiment. (B) Before mixing CD4$^+$CD25$^-$ and CD4$^+$CD25$^+$ T cells at a 1:1 ratio, CD4$^+$CD25$^+$ T cells were labeled with CFSE (0.5 µM) for 15 min. Cells were then mixed and stimulated with immobilized anti-CD3/soluble anti-CD28. After 48 h cells were harvested and sorted on a FACS Vantage®. The positive and the negative fraction were then cocultured with syngeneic resting CD4$^+$CD25$^-$ T cells ($10^5$ T cells per 96 well). Proliferation was measured after 5 d by [$^3$H]Tdr incorporation. One out of 5 independent experiments is shown.

DETAILED DESCRIPTION OF THE INVENTION

The important in vivo function of CD4$^+$CD25$^+$ regulatory T cells has been thoroughly demonstrated in rodents (Asano et al., *J. Exp. Med.* 184:387-396 (1996); Takahashi et al., *Int. Immunol.* 10:1969-1980 (1998); Thornton et al., *J. Exp. Med.* 188:287-296 (1998)). Recent studies demonstrate, that CD4$^+$CD25$^+$ T cells are also relevant as an immune regulator in humans (Jonuleit et al., *J. Exp. Med.* 193:1285-1294 (2001); Levings et al., *J. Exp. Med.* 193:1295-1302 (2001); Dieckmann et al., *J. Exp. Med.* 193:1303-1310 (2001); Taylor et al., *J. Exp. Med.* 193:1311-1318 (2001)). Lately we and others have shown that a similar population of regulatory T cells also exists in humans (PCT/EP02/02671). These findings have been confirmed and extended by several groups up to now (Jonuleit et al., *J. Exp. Med.* 193:1285-1294 (2001); Levings et al., *J. Exp. Med.* 193:1295-1302 (2001); Dieckmann et al., *J. Exp. Med.* 193:1303-1310 (2001); Taylor et al., *J. Exp. Med.* 193:1311-1318 (2001); Nakamura et al., *J. Exp. Med.* 194:629-644 (2001); Ng et al., *Blood* 98:2736-2744 (2001); Iellenn et al., *J. Exp. Med.* 194:847-853 (2001); Yamagiwa et al., *J. Immunol.* 166:7282-7289 (2001); Stephens et al., *Eur. J. Immunol.* 31:1247-1254 (2001); Taams et al., *Eur. J. Immunol.* 31:1122-1131 (2001)). Still numerous characteristics of CD4$^+$CD25$^+$ T cells need to be explained. One important question that has to be answered is how CD4$^+$CD25$^+$ T cells execute their important function in vivo, as they only constitute a small population of peripheral CD4$^+$ T cells (average 6%), that need direct cell contact as well as stimulation via the TCR to suppress unwanted T cell activation. In vitro studies usually employ high ratios of CD4$^+$CD25$^+$/CD4$^+$CD25$^-$ T cells, a situation that is hard to imagine at an inflammatory site in vivo. As described, coculture of CD4$^+$CD25$^+$ and CD4$^+$CD25$^-$ T cell leads to marked reduction of T cell proliferation (Dieckmann et al., *J. Exp. Med.* 193:1303-1310 (2001)). This effect is stable for several days (data not shown). Although CD4$^+$CD25$^+$ T cells produce sizeable quantities of IL-10 this cytokine does not seem to be responsible for the regulatory effects (Dieckmann et al., *J. Exp. Med.* 193:1303-1310 (2001)). The supernatant of CD4$^+$CD25$^+$ and CD4$^+$CD25$^-$ cocultures were analyzed and it was found that high levels of IL-10 are produced, peaking after 48 h. IL-10 levels in the coculture were markedly higher than IL-10 produced by CD4$^+$CD25$^+$ T cells alone, suggesting that it was not only attributable to CD4$^+$CD25$^+$ T cells. This was further confirmed by intracellular FACS® analysis. IL-10 is known to inhibit cytokine production from T cells (Moore et al., *Science* 248:1230-1234 (1990)) and exert anti-inflammatory and suppressive effects on most haematopoeitic cells. It is also involved in the induction of peripheral tolerance via effects on T-cell-mediated responses (Moore et al., *Science* 248:1230-1234 (1990)). IL-10 indirectly suppresses T-cell responses by potently inhibiting the antigen-presenting capacity of APC, including DC (Steinbrink et al., *J. Immunol.* 159:4772-4780 (1997), Langerhans cells and macrophages (Romagnoli et al., *J. Immunol.* 168:1644-1648 (2002)). In addition, IL-10 directly regulates T cells by inhibiting their ability to produce IL-2, TNF-α (De Waal et al., *J. Immunol.* 150:4754-4765 (1993)), IL-5 (Schandene et al., *J. Immunol.* 152:4368-4374 (1994)) and to proliferate Bejarano et al., *Int. Immunol.* 4:1389-1397 (1992)). It was important to rule out, that the effects seen were not only due to CD4$^+$CD25$^+$ T cells in the coculture. In a set of pilot experiments we could show, that CD4$^+$CD25$^+$ T cells when paraformaldehyde-fixed after polyclonal activation have similar regulatory properties as viable CD4$^+$CD25$^+$ T cells. In coculture experiments, employing activated-fixed and viable CD4$^+$CD25$^+$ T cells together with CD4$^+$CD25$^-$ T cells, it turned out, that IL-10 production remained high, even if activated-fixed CD4$^+$CD25$^+$ T cells were used. This showed, that IL-10 production was not attributable to increased production by CD4$^+$CD25$^+$ but due to the anergized CD4$^+$CD25$^-$ T cells. In a parallel transwell approach we showed, that direct cell contact between CD4$^+$CD25$^+$ and CD4$^+$CD25$^-$ T cells is necessary to prime CD4$^+$CD25$^-$ T cells to become IL-10 producers.

Further experiments were performed to analyze, which effect this high level of IL-10 might have on T cell proliferation. Indeed it was shown, that proliferation of syngeneic CD4$^+$ T cells could be markedly decreased by anergized CD4$^+$CD25$^-$ T cells. Addition of anti-IL-10 abolished the suppressive effects of anergized CD4$^+$CD25$^-$ T cells, while a transwell setting, permitting the free exchange of soluble factors, but no cell contact, did not change suppression. Furthermore, we CSFE-labeled CD4$^+$CD25$^+$ T cells and separated them from CD4$^+$CD25$^-$ T cells after 48 h of coculture by FACS® sorting. Both populations strongly inhibited CD4$^+$ T cell proliferation which was almost abolished in the unlabeled e.g. CD4$^+$CD25$^-$ fraction by the addition of anti-IL-10, demonstrating that IL-10 indeed is crucial for the suppressive function of energized CD4$^+$CD25$^-$ T cells. This is not surprising, as other reports have shown, that activation of human CD4$^+$ T cells in the presence of IL-10 results in a state of functional unresponsiveness without death, termed anergy (Iellenn et al., *J. Exp. Med.* 194:847-853 (2001)). CD4$^+$ T cells with low proliferative capacity, that are generated in the presence of IL-10 have been termed type 1 T regulatory cells (Tr1). The cells that are generated in the presence of CD4$^+$CD25$^+$ T cells show some characteristics resembling Tr1 cells, especially their low proliferative capacity and the high level production of IL-10. But in some instances they differ, as Tr1 are also defined by their ability to produce TGF-β and anergized CD4$^+$CD25$^-$ T cells did not produce significant amounts of TGF-β at least by the assay used. Further on we clearly demonstrate, that cell contact between CD4$^+$CD25$^+$ and CD4$^+$CD25$^-$ T cells and not IL-10 is crucial for the induction phase of inhibitory, anergized, IL-10-producing, CD4$^+$CD25$^-$ T cells. But as coculture of anergized CD4$^+$CD25$^-$ with syngeneic resting CD4$^+$CD25$^-$ T cells results in anergic, IL-10 releasing CD4$^+$CD25$^-$ T cells this IL-10 production may then also contribute to the generation of Tr1-like cells as described for Tr1 cells. To distinguish between indirect effects via APC modulation and direct effect on T cells we used as a stimulus not only allogeneic DC but also immobilized anti-CD3/soluble anti-CD28 as a cell free T cell stimulation system. As the effects seen were independent of the stimuli used, a direct effect on T cells is most likely. The data presented here may serve as an explanation of how CD4$^+$CD25$^+$ T cells fulfill their important in vivo function. At sites of inflammation if activated they would anergize CD4$^+$ T cells in their lose environment in an antigen-unspecific bystander effect fashion (Thornton et al., *J. Immunol.* 164: 183-190 (2000)). Our findings suggest, however, that anergized CD4$^+$ T cells (including pathogenic ones) in turn will produce high levels of IL-10 thereby creating an immunosuppressive environment either by indirect effect via influence on APC (Steinbrink et al., *Blood* 93:1634-1642 (1999)) or via direct effects on other T cells thereby effectively abrogating unwanted T cell activation.

The invention is further explained by the following examples, which are, however, not to be construed as to limit the invention.

EXAMPLES

Abbreviations

CFSE, 5-carboxyfluorescein diacetat succinimdyl ester; CTLA-4, cytotoxic T lymphocyte antigene 4; DC, dendritic cell; MACS®, magnetic activated cell sorting; Tr1, T regulatory cell 1.

Material and Methods

Culture Medium:

RPMI 1640 (Bio Whittaker) supplemented with 1% heat-inactivated autologous plasma, 20 µg/ml gentamicin (Merck) and 2 mM glutamine (Bio Whittaker) was used for the generation of dendritic cells (DC), X-VIVO-20 (Bio Whittaker) supplemented with 1% heat-inactivated single donor human serum, 20 µg/ml gentamicin (Merck) and 2 mM glutamine (Bio Whittaker) for T cell culture.

Cytokines:

All cytokines used in this study were recombinant human proteins. Final concentrations were: GM-CSF 1,000 U/ml (Leukomax™; Novartis), IL-4 800 U/ml (Sandoz) and IL-2 (Proleukin; Chiron Corp.) were used at the concentrations indicated; for DC maturation we used a cocktail consisting of IL-1β 2 ng/ml (Sigma); IL-6 1000 U/ml (Sandoz); TNF-α 10 ng/ml (Bender, Vienna), and PGE$_2$ 1 µg/ml (Sigma).

Antibodies:

For immunostaining PE- and FITC-conjugated Antibodies (Ab) (all from BD Pharmingen) against CD3 (UCHT 1), CD4 (RPA-T4), CD5 (UCHT 2), CD8 (RPA-T8), CD14 (M5E2), CD19 (HIB 19), CD25 (M-A251), CD28 (CD28.2), CD45 RA (HI 100), CD45 RO (UCHL 1), CD56 (B159), CD62L (DREG-56), CD80 (L307.4), CD83 HB15e), CD86 (FUN-1), CD95 (DX 2), CD95L (G247-4), CD122 (MiK-132), CD152 (BNI3.1), CD154 (TRAP1), HLA-DR (G46-6), and respective mouse and rat isotype controls were employed. Ab used for intracellular cytokine staining were FITC- and PE-conjugated anti-IL-2 (MQ1-17H12), anti-IL-4 (8D4-8), anti-IL-10 (JES3-19F1) and anti-IFN-γ (4S.B3), all from BD Pharmingen. Unconjugated anti-IL-10 (JES3-19F1) (Pharmingen) was used for neutralization experiments, anti-CD3 (UCHT1) and anti-CD28 (CD28.2) for polyclonal activation of T cells.

Cytokine Assays:

T cells were stimulated with allogeneic DC or with platebound anti-CD3 (10 µg/ml)+soluble anti-CD28 (10 µg/ml) in X-VIVO-20+1% serum. Cytokine analysis was performed at different time points by analysis of supernatants with commercially available ELISA kits for human IL-10, IFN-α (Biosource International) and TGF-β (BD Pharmingen). IL-2, IL-4, IL-5, IFN-γ and TNF-α were measured by a cytometric bead array (Th1/Th2 Cytokine CBA 1; BD Pharmingen) according to the manufacturers instructions. For analysis of intracellular cytokine production T cells were either stimulated with PMA 20 ng/ml and Ca 2+ ionophore A23187 500 µg/ml (both from SIGMA) for 6 hours or with platebound anti-CD3 and soluble anti-CD28 Ab for 6 hours. Monensin, 2 µM (SIGMA) was added for the last 5 hours of culture. Cells were collected, washed, fixed and saponine permeabilized (Fix/perm solution, BD Pharmingen) and stained with cytokine specific Ab or isotype.

Cell Isolation and DC Generation:

DC were generated from buffy coats orleukapheresis products (both obtained from the Department of Transfusion medicine, University of Erlangen, from healthy donors after informed consent was given) as described in Romani et al, *J. Immunol. Methods* 196:137-151(1996) and Thurner et al., *J. Immunol. Methods* 223:1-15(1999). In brief, PBMCs were isolated by Ficoll density gradient centrifugation. Monocytes were isolated by plastic adherence and cultured in RPMI Medium, supplemented with IL-4 and GM-CSF. At day 6, a maturation cocktail (IL-1β, IL-6, PGE$_2$ and TNFα) was added. At day 7 nonadherend cells were harvested and constituted mature DC that were >90% double positive for costimulatory molecules (CD80, CD86) and CD83.

CD4$^+$ T cells were isolated from PBMC with a negative CD4$^+$ T cell isolation kit (Miltenyi Biotech). CD4$^+$CD25$^+$ T cells were isolated from the pure, untouched CD4$^+$ T cells using CD25 Microbeads (Miltenyi Biotech). Purity was assessed by FACS®.

Flow Cytometric Analysis:

For immunofluorescence staining cells were washed and stained for 20 min at 4° C. with optimal dilution of each Ab. Cells were washed again and analyzed by flow cytometry (FACS Scan® and CELLQuest® software; Becton Dickinson). For analysis of intracellular CD152 cells were stained for CD4 expression, fixed and saponine permeabilized (Fix/perm solution, BD Pharmingen) and stained with CD152 specific Ab or isotype.

Fixation of CD4$^+$CD25$^+$ and CD4$^+$CD25$^-$ T Cells:

For fixation experiments CD4$^+$CD25$^+$ and CD4$^+$CD25$^-$ T cells were isolated and divided into three fractions. One part of each was activated with platebound anti-CD3 and soluble anti-CD28 over night. Next day the stimulated parts and one resting part were fixated with 2% paraformaldehyde for 1 h at 4° C. Thereafter fixated cells were washed extensively and used in regulation assays together with the untreated fraction.

Induction of Anergized T Cells:

To induce anergized CD4$^+$CD25$^-$ T cells with CD4$^+$CD25$^+$ T cells, both populations were isolated as described. They were either used directly or fixated as described above. 5×10$^5$ of CD4$^+$CD25$^+$ and CD4$^+$CD25$^-$ T cells were cultivated either with platebound anti-CD3 and soluble anti-CD28 (10 µg/ml each) or with allogeneic mature DC (5×10$^4$) for 48 h in 48 well plates. Thereafter cells were harvested, washed and used in proliferation experiments.

Proliferation Assays:

To assess proliferation of the differently cultured CD4$^+$ subtypes 10$^5$ sorted T cells were incubated in X-VIVO-20 with 5×10$^3$ DC in 96-well U-bottom plates or 10 µg/ml of platebound anti-CD3+10 µg/ml soluble anti-CD28 in 96-well flat-bottom plates. For assessment of regulatory properties 10$^5$ resting CD4$^+$CD25$^-$ autologous T cells were cultured with 5×10$^3$ DC or platebound anti-CD3 and soluble anti-CD28 in 96-well U-bottom plates. Purified CD4$^+$CD25$^+$ and CD4$^+$CD25$^-$ T cells, anergized CD4$^+$CD25$^-$ T cells or fixated CD4$^+$CD25$^+$ and CD4$^+$CD25$^-$ T cells were added usually at a 1:1 ratio, if not indicated differently. After 4-5 days of culture [$^3$H]Tdr (37 kBq/well) was added for additional 16 h. Proliferation was measured using a liquid scintillation counter.

Transwell Experiments:

Transwell experiments were performed in 24-well plates. $10^6$ CD4$^+$CD25$^-$ T cells were stimulated with 5×10$^4$ DC. In addition, $10^6$ CD4$^+$CD25$^+$, CD4$^+$CD25$^-$ and anergized CD4$^+$CD25$^-$ T cells were either added directly to the culture or were placed in transwell chambers (Millicell, 0.4 μm; Millipore). After 5 days of coculture T cells were transferred to 96-well plates ($10^5$ cells/well) in triplicates. Proliferation was measured after 16 h pulse with [$^3$H]Tdr using a liquid scintillation counter.

CFSE Labeling and Sorting:

CD4$^+$CD25$^+$ and CD4$^+$CD25$^-$ T cells were labeled with 0.5 μM of CFSE (Molecular Probes) for 15 minutes at 37° C. Reaction was stopped with ice-cold PBS buffer and cells were washed extensively. 5×10$^5$ CD4$^+$CD25$^+$CFSE labeled T cells were then cultured with 5×10$^5$ unlabeled CD4$^+$CD25$^-$ T cells (and vice versa) with platebound anti-CD3 and soluble anti-CD28 in 48 well plates. Proliferation was controlled by FACS® for different time points. After 48 h cells were harvested and sorted on a FACS Vantage® (Becton Dickinson). Sorted cells were used for further regulation assays.

Example 1

Figure 1:
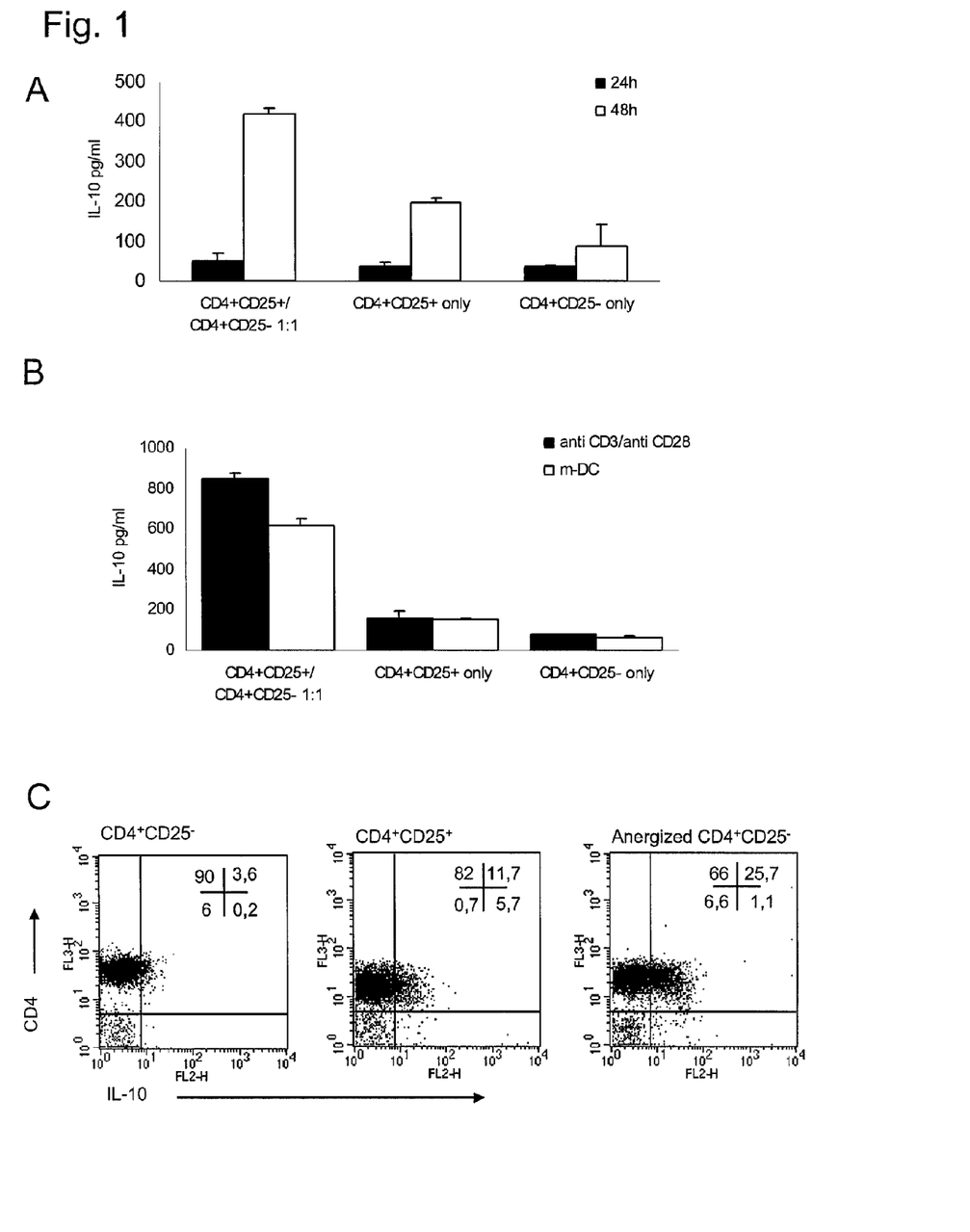
FIG. 1: Coculture of CD4$^+$CD25$^+$ and CD4$^+$CD25$^-$ T cells results in high level IL-10 production. CD4$^+$CD25$^+$ and CD4$^+$CD25$^-$ T cells were MACS® sorted from PBMC of healthy individuals. These cells were either cultured alone or at a 1:1 ratio and activated with platebound anti-CD3 and soluble anti-CD28 (10 µg/ml respectively).
Figure 2:
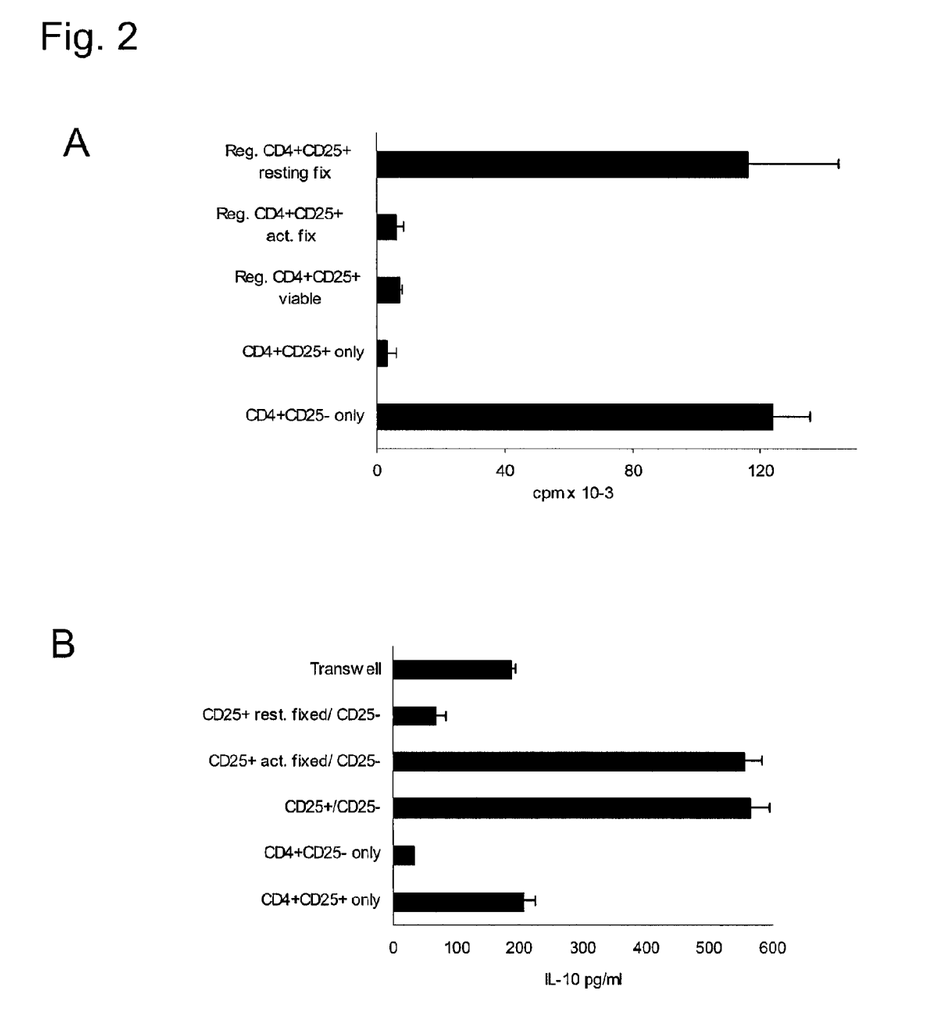
FIG. 2: Activated fixed CD4$^+$CD25$^+$ T cells show similar regulatory potential as viable CD4$^+$CD25$^+$ T cells and can induce IL-10 production in CD4$^+$CD25$^-$ T cells.

Coculture of CD4$^+$CD25$^+$ and CD4$^+$CD25$^-$ T Cells Yields Low Proliferating, IL-10 Producing T Cells CD4$^+$CD25$^+$ and CD4$^+$CD25$^-$ subpopulations were separated by magnetic cell sorting from healthy donors. Separately or mixed at a 1:1 ratio the cells were stimulated polyclonally with platebound anti-CD3 and soluble anti-CD28 or with mature allogeneic DC. As shown before coculture of CD4$^+$CD25$^+$ and CD4$^+$CD25$^-$ T cells results in a constantly low proliferating T cell population (data not shown). The supernatant of this coculture was analyzed after various time points for different cytokines and a high level of IL-10 production was found (peaking 48 h after onset of culture (FIG. 1A)). As shown before CD4$^+$CD25$^+$ T cells alone also produce sizeable amounts of IL-10 (~200 pg/ml). One might speculate, that IL-10 production was only attributable to CD4$^+$CD25$^+$ T cells, but IL-10 production in the coculture was 2-4 times higher then production of CD4$^+$CD25$^+$ T cells alone (FIGS. 2A & B). Intracellular FACS revealed, that the number of IL-10 producing cells more then doubled (FIG. 1C). High IL-10 production after 48 h of coculture was observed regardless if polyclonal activation (platebound anti-CD3 and soluble anti-CD28) or allogeneic mature DC were used (FIG. 1B). In none of the cultures increased production of TGF-β or Inf-α could be observed (data not shown). CD4$^+$CD25$^-$ T cells alone did not produce significant amounts of IL-10 (FIG. 1A-C)

Example 2

Activated, Paraformaledhyd-Fixed CD4+CD25+T Cells Show Similar Regulatory Capacity as Viable Cells It is known, that CD4$^+$CD25$^+$ T cells exert their regulatory function in a cell contact-dependent yet cytokine-independent manner. To further analyze their regulatory function, isolated CD4$^+$CD25$^+$ T cells were divided into three parts. One was activated over night polyclonally with platebound anti-CD3 and soluble anti-CD28 and fixed thereafter with paraformaldehyde ("activated-fixed"), the second part was fixed with paraformaldehyde without prior activation ("resting-fixed") and the third part was left untreated ("viable").

After this procedure the three differently treated fractions of CD4$^+$CD25$^+$ T cells were used in regulation assays with syngeneic CD4$^+$CD25$^-$ T cells. As shown in FIG. 2A activated-fixed CD4$^+$CD25$^+$ T cells had a similar regulatory capacity as their normal viable counterpart. This is in sharp contrast to resting-fixed CD4$^+$CD25$^+$ T cells which do not show any regulatory function at all.

Activated-fixed and viable CD4$^+$CD25$^+$ T cells almost completely suppressed proliferation of CD4$^+$CD25$^-$ T cells when a 1:1 ratio was used. This underlines and extends prior findings on the regulatory function, demonstrating that surface molecules, induced after activation of CD4$^+$CD25$^+$ are responsible for the regulatory capacity of these cells.

Example 3

CD4$^+$CD25$^+$ Regulatory T Cells Induce IL-10 Production in Anergized CD4$^+$CD25$^-$ T Cells in a Cell Contact-Dependent Manner In further experiments the above mentioned findings were used to analyze the requirements for induction of IL-10 producing anergized CD4$^+$CD25$^-$ T cells. CD4$^+$CD25$^+$ and CD4$^+$CD25$^-$ T cells were either cultured alone or at a 1:1 ratio with normal viable CD4$^+$CD25$^+$ T cells, activated-fixed CD4$^+$CD25$^+$ T cells, resting-fixed CD4$^+$CD25$^+$ T cells or in a transwell setting. IL-10 production was measured 48 h after onset of culture. As shown in FIG. 2B a high level IL-10 production was achieved in coculture either with viable CD4$^+$CD25$^+$ or activated-fixed CD4$^+$CD25$^+$ T cells. In Transwell experiments IL-10 production, similar to that of CD4$^+$CD25$^+$ T cells alone was observed and CD4$^+$CD25$^-$ T cells alone produced negligible amounts of IL-10.

Example 4

Figure 3:
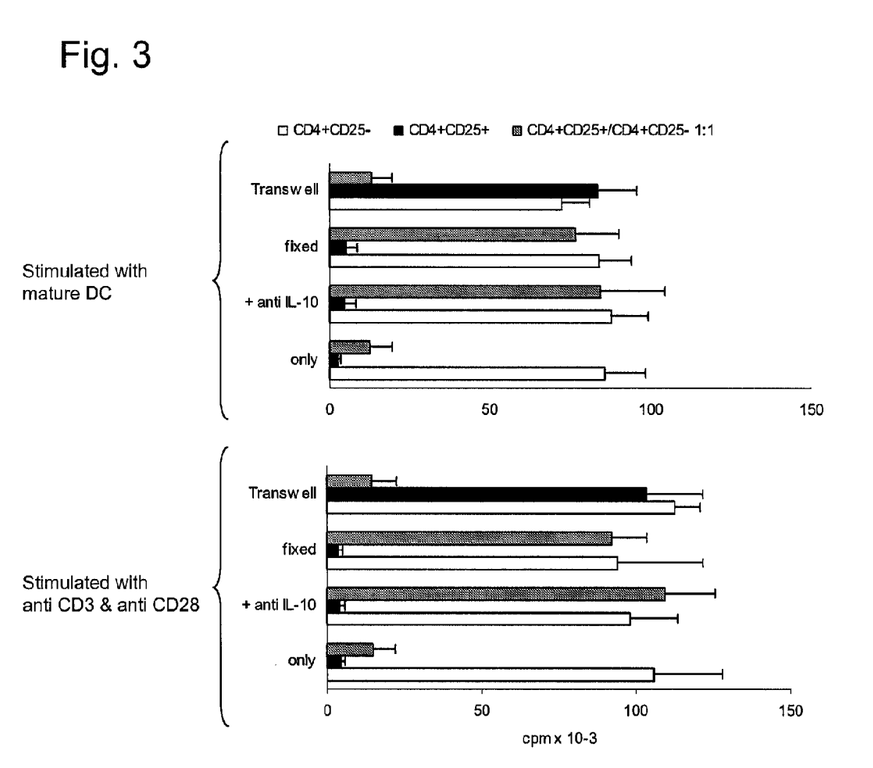

CD4+CD25−T Cells Anergized by CD4+CD25+T Cells Suppress Activation of Syngeneic CD4+T Cells in an IL-10 Dependent Manner IL-10 is known as a cytokine with potent immunosuppressive function. It was therefore tempting to speculate, that the high IL-10 production of anergized CD4$^+$CD25$^-$ T cells would lead to secondary suppression of other T cells. In a next set of experiments we sought to investigate this matter. As it is known, that IL-10 can act indirectly on T cells, via influence on APC, we choose a polyclonal, cell free T cell stimulus (platebound anti-CD3 and soluble anti-CD28) and mature allogeneic DC, because they are known as the most powerful APC and largely resistant to IL-10 17. CD4$^+$CD25$^+$ and CD4$^+$CD25$^-$ T cells alone or at a 1:1 ratio were stimulated with allogeneic DC (FIG. 3, upper panel) or with bound anti-CD3 and soluble anti-CD28 (FIG. 3, lower panel) for 48 h. Thereafter cells were either fixed with paraformaldehyde or used viable. As expected activated CD4$^+$CD25$^+$ T cells induced strong suppression of CD4$^+$ proliferation and at a 1:1 ratio almost abolished it, whereas activated CD4$^+$CD25$^-$ T cells did not alter proliferation of syngeneic CD4$^+$ T cells. When the cocultured CD4$^+$CD25$^+$ and CD4$^+$CD25$^-$ T cells were used in regulation assays, they mediated a strong inhibition of CD4$^+$ T cell proliferation (FIG. 3). This phenomenon was seen, regardless of the stimulus used (FIG. 3, upper and lower panel). We further added anti-IL-10 Ab to the regulation assay or performed it in a transwell setting. As shown before anti-IL-10 did not alter suppressive function of pure CD4$^+$CD25$^+$ T cells, whereas in a transwell setting CD4$^+$CD25$^+$ T cells could not mediate suppression. The opposite was true for regulation by anergized CD4+CD25− T cells. Addition of IL-10 antibodies almost completely abolished inhibition, whereas a transwell setting did not markedly change the regulatory function of these cells. Suggesting, that inhibition is mediated dominantly by secretion of IL-10 (FIG. 3). Similar effects were seen with polyclonally or allogeneic stimulated cells (FIG. 3, upper and lower panel).

Figure 4:
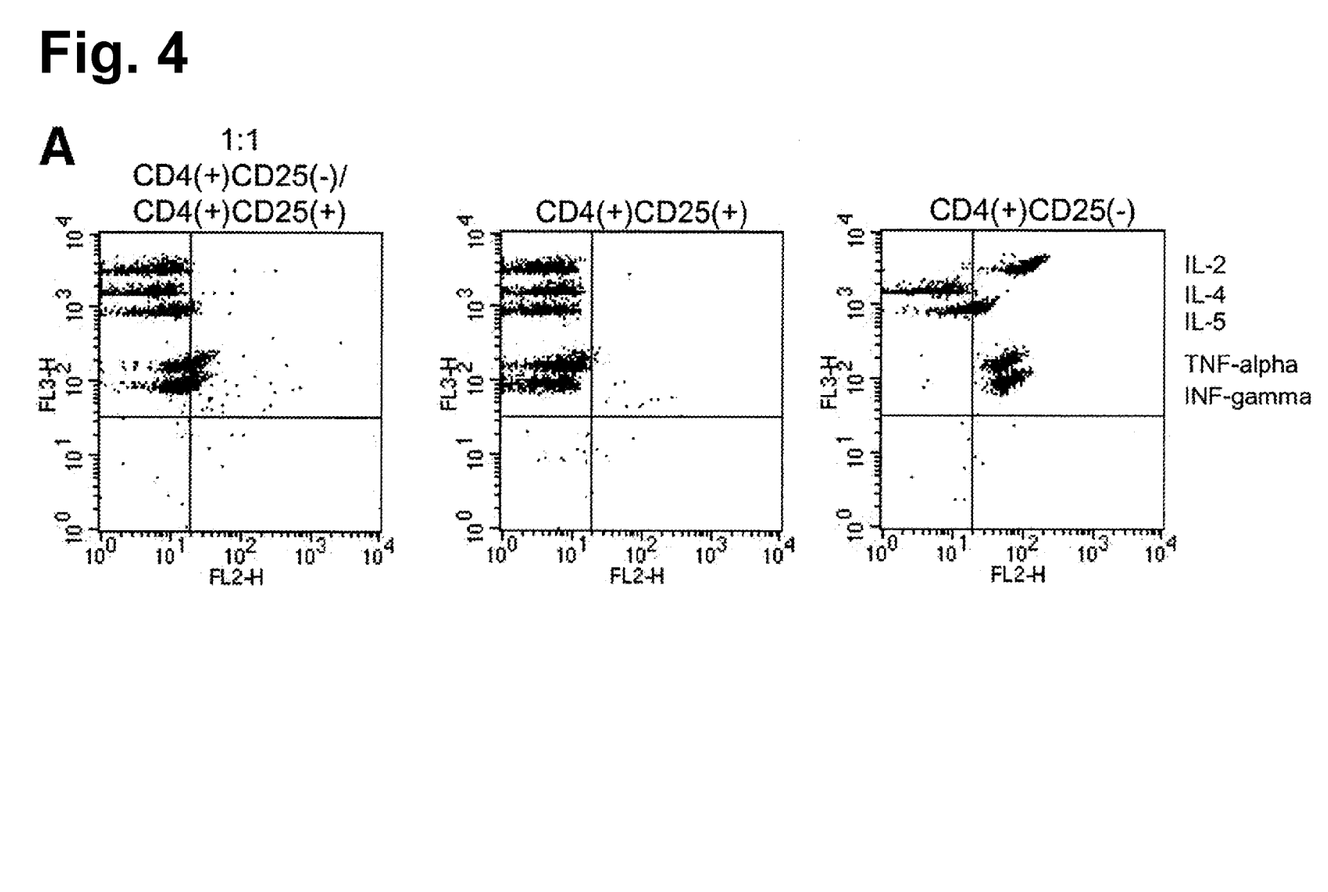

To further exclude that the observed effects are mediated by CD4+CD25+ T cell directly we performed CFSE labeling and FACS® sorting experiments. CD4+CD25− T cells were labeled with CFSE and then mixed with CD4+CD25+ unlabelled T cells at 1:1 ratio. This mixture was stimulated with immobilized anti-CD3/soluble anti-CD28 for 48 h. Thereafter cells were sorted by FACS® and used in regulation assays with syngeneic CD4+CD25− T cells. As shown in FIG. 4, regulation was mediated by both, the labeled and unlabeled fractions, which was abolished by addition of anti-IL-10 in the case of unlabeled (anergized CD4+CD25− T cells). Not surprisingly activated CD4+CD25+ T cells showed inhibition of T cells proliferation themselves. This could not be abolished by anti IL-10, clearly demonstrating, that anergized CD4+CD25− T cells mediate suppression via IL-10 which is distinct from the mechanisms utilized by CD4+CD25+ T cells.

Example 5

Anergized CD4+CD25− T Cells Predominantly Produce IL-10

To analyze the cytokine secretion pattern of anergized CD4+CD25− T cells, CD4+CD25+ and CD4+CD25− T cells were sorted and stimulated alone or at a 1:1 mixture as described before. After 48 hours of culture supernatants were analyzed for the cytokines IL-2, IL-4, IL-5, TNF-α and INF-γ by a cytometric bead array, which allows multiparameter analysis in a single sample. As shown in FIG. 4, anergized CD4+CD25− T cells similar to CD4+CD25+ T cells do only produce very low levels of TNF-α and INF-γ and no IL-2, -4 or IL-5. CD4+CD25− T cells on the other hand produce high levels of IL-2, TNF-α and INF-γ and low to moderate levels of IL-4 and IL-5, resembling a TH1 phenotype. Surface phenotyping with the Abs mentioned in material and method did not reveal striking differences between activated CD4+CD25+, activated CD4+CD25− and cocultured CD4+CD25+/CD4+CD25− T cells after 48 h of activation (data not shown).

The invention claimed is:

1. A method of suppressing the proliferation of human CD4+ T cells ex vivo or in vivo comprising the steps of:
    (a) isolating CD4+CD25+ T cells from human peripheral blood;
    (b) anergizing human CD4+CD25− T cells by contacting the CD4+CD25− T cells ex vivo with an anergic state inducing agent consisting of the CD4+CD25+ T cells and an activation stimulus, whereby Tr-1 like regulatory cells are produced, wherein the activation stimulus is selected from the group consisting of (i) and (ii), wherein (i) is a combination of anti-CD3 and anti-CD28 antibodies; and (ii) is mature dendritic cells; and
    (c) suppressing the proliferation of said CD4+ T cells by (i) introducing said Tr-1 like regulatory cells to a composition comprising said CD4+ T cells ex vivo or (ii) administering said Tr-1 like regulatory cells to a human subject in vivo.

2. The method of claim 1, wherein step (b) of the method of producing said Tr-1 like regulatory cells comprises co-culturing the CD4+CD25− cells with CD4+CD25+ cells ex vivo and wherein said Tr1-like regulatory cells produce IL-10.

3. The method of claim 1, wherein said Tr-1 like regulatory cells are administered to a human subject.

4. The method of claim 3, wherein said administration is to treat graft versus host disease in said human subject.

* * * * *

UNITED STATES PATENT AND TRADEMARK OFFICE
CERTIFICATE OF CORRECTION

PATENT NO.      : 8,603,815 B2                                        Page 1 of 1
APPLICATION NO. : 13/289409
DATED           : December 10, 2013
INVENTOR(S)     : Schuler et al.

It is certified that error appears in the above-identified patent and that said Letters Patent is hereby corrected as shown below:

In the Specification

Column 5, line 36, "Iellenn" -- should read -- Iellem --.

Column 6, line 42, "Iellenn" -- should read -- Iellem --.

Signed and Sealed this
Twentieth Day of October, 2015

Michelle K. Lee
*Director of the United States Patent and Trademark Office*